United States Patent [19]

Steiner et al.

[11] 4,399,137

[45] Aug. 16, 1983

[54] 6-IMIDAZOL-1-YL-3-HYDRAZINO-PYRIDAZINES, THEIR PREPARATION AND ANTIHYPERTENSIVE USE

[75] Inventors: Gerd Steiner, Kirchheim; Josef Gries, Wachenheim; Dieter Lenke, Ludwigshafen, all of Fed. Rep. of Germany

[73] Assignee: BASF Aktiengesellschaft, Fed. Rep. of Germany

[21] Appl. No.: 330,374

[22] Filed: Dec. 14, 1981

Related U.S. Application Data

[63] Continuation of Ser. No. 176,018, Aug. 7, 1980, abandoned.

[30] Foreign Application Priority Data

Sep. 1, 1979 [DE] Fed. Rep. of Germany ....... 2935359

[51] Int. Cl.³ .................... C07D 403/04; A61K 31/50
[52] U.S. Cl. .................................... 424/250; 544/238
[58] Field of Search ......................... 544/238; 424/250

[56] References Cited

U.S. PATENT DOCUMENTS

| | | |
|---|---|---|
| 4,026,891 | 5/1977 | Austel .................................. 544/238 |
| 4,134,983 | 1/1979 | Baldwin .............................. 544/238 |
| 4,224,325 | 9/1980 | Szilagyi ............................... 544/238 |
| 4,251,658 | 2/1981 | Szilagyi et al. ..................... 544/238 |

OTHER PUBLICATIONS

Steiner et al., Chem. Abs. 94, 30688p (1981).
Szilagyi et al., European J. Med. Chem. 14, 438–445 (1979).

*Primary Examiner*—Mark L. Berch
*Attorney, Agent, or Firm*—Keil & Witherspoon

[57] ABSTRACT

6-Imidazol-1-yl-3-hydrazino-pyridazines, in which the imidazole ring is unsubstituted or is substituted by halogen or alkyl, their physiologically tolerated addition salts with acids, processes for their preparation and their use as drugs in the treatment of hypertonia.

5 Claims, No Drawings

6-IMIDAZOL-1-YL-3-HYDRAZINO-PYRIDAZINES, THEIR PREPARATION AND ANTIHYPERTENSIVE USE

This is a continuation of application Ser. No. 176,018, filed Aug. 7, 1980, abandoned.

The present invention relates to 6-imidazol-1-yl-3-hydrazino-pyridazines in which the imidazole ring is unsubstituted or is substituted by halogen or alkyl, their physiologically tolerated addition salts with acids, processes for their preparation and their use as drugs in the treatment of hypertonia.

3-Hydrazino-pyridazines which are substituted in the 6-position by a pyrazolyl ring have been disclosed in Eur. J. Med. Chem. 14, (1979). 438–445, as compounds which lower the blood pressure.

We have found that 6-imidazolyl-3-hydrazinopyridazines of the general formula I

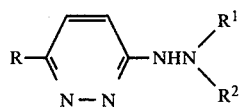

where R is an imidazol-1-yl radical which is unsubstituted or possesses one or two halogen substituents or one, two or three $C_1$–$C_3$-alkyl substituents and $R^1$ and $R^2$ are each hydrogen or together are a radical

where $R^3$ and $R^4$ are each alkyl of 1 to 4 carbon atoms or alkenyl of 2 to 5 carbon atoms, and their physiologically tolerated addition salts with acids, possess valuable pharmacological properties, in particular a pronounced blood pressure-lowering action.

Halogen substituents in the imidazole radical are in particular chlorine. Preferred compounds are in particular those containing 2-alkyl-imidazol-1-yl radicals. Specific examples of such radicals are 2-methyl-imidazol-1-yl, 2-ethyl-imidazol-1-yl, 4-methyl-imidazol-1-yl, 2,4,5-trimethyl-imidazol-1-yl and 2-isopropyl-imidazol-1-yl.

Amongst compounds of the formula I which contain the radical

those where $R^3$ and $R^4$ are each methyl and those where $R^3$ is methyl and $R^4$ is 2-methyl-prop-1-enyl are particularly important.

To prepare a compound of the formula I, the alkali metal salt or alkaline earth metal salt of an imidazole which is unsubstituted at the N-atom 1 and corresponds to the radical R in the formula I is reacted with 3,6-dichloropyridazine in a high-boiling polar aprotic solvent at from 20° to 170° C. and the product is then reacted with hydrazine hydrate, in the presence or absence of a solvent, at from 80° C. to the reflux temperature of the reaction mixture, to give a 6-(imidazol-1-yl)-3-hydrazino-pyridazine of the general formula I, which may or may not then be reacted with a carbonyl compound of the formula

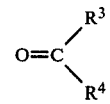

where $R^3$ and $R^4$ have the above meanings, to give a hydrazone. If desired, the compound obtained, of the formula I, may be converted to an addition salt with a physiologically tolerated acid.

The reaction is illustrated by the following equation:

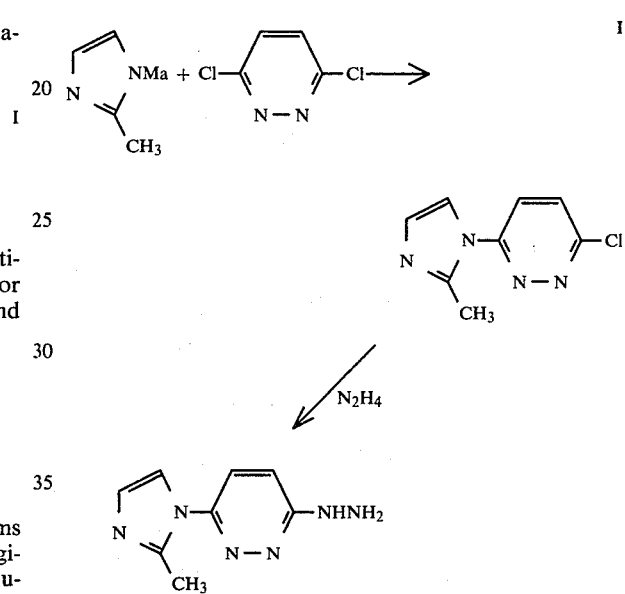

Advantageously, the imidazole is converted to an alkali metal salt or alkaline earth metal salt by adding an equivalent amount of a strong base which is capable of reaction with the imidazole to form a salt. Examples of suitable bases are alkali metal hydrides and amides, alkaline earth metal hydrides and amides, and organometallic compounds; sodium hydride is preferred. The formation of the salt is advantageously carried out in a high-boiling polar aprotic solvent, preferably dimethylformamide, by stirring for from half to two hours at from 20° to 80° C., advantageously under an inert gas atmosphere. 1 mole equivalent of 3,6-dichloro-pyridazine is then reacted with the product, at from 20° to 170° C., as a rule for from 3 to 10 hours, to give the corresponding 3-chloro-6-(imidazol-1-yl)-pyridazine.

The 3-chloro-6-imidazolyl-pyridazine may advantageously be purified in a conventional manner by column chromatography over silica gel, using a mixture of methylene chloride and methanol (70–90: 30–10 parts by volume) as the eluant.

The 3-chloro-6-(imidazol-1-yl)-pyridazine obtained is then reacted with excess hydrazine hydrate, in the presence or absence of a polar protic solvent, eg. ethanol, isopropanol or methanol, for from 3 to 6 hours at from 80° C. to the boiling point, to give the novel 6-(imidazol-1-yl)-3-hydrazinopyridazines of the formula I.

The end product may be purified by recrystallization from a lower alcohol, or by column chromatography.

The novel compounds of the general formula I, where R¹ and R² are

are obtained by converting the free hydrazine into the corresponding hydrazone in a conventional manner, as illustrated by the following equation:

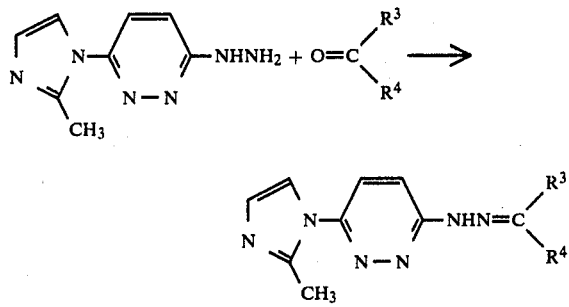

A 6-(imidazol-1-yl)-3-hydrazino-pyridazine is condensed in a known manner with a suitable carbonyl compound, eg. acetone, acetaldehyde, benzaldehyde, furfural, mesityl oxide, diallyl ketone or the like, to give the corresponding hydrazone, in the presence or absence of a lower alcohol, especially ethanol, as the solvent, and in the presence of a catalytic amount of an acid, eg. acetic acid or hydrochloric acid.

The compounds according to the invention are in general obtained as colorless to yellowish brown crystals and can be recrystallized from conventional organic solvents, preferably from isopropanol or ethanol, or be purified by column chromatography, as described above for the case of the intermediates. The novel compounds form non-toxic addition salts with pharmacologically tolerated inorganic and organic acids. The addition salts are obtained in a conventional manner, for example by adding one or two equivalents of an acid to the free base, preferably in a neutral solvent.

Suitable physiologically tolerated acids are listed, for example, in Fortschritte der Arzneimittelforschung, volume 10, pages 224–225, Birkhäuser Verlag, Basel and Stuttgart, 1966, or J. Pharmac. Sci., 66 (1977), 1–5.

Examples of the novel compounds, in addition to those mentioned in the Preparative Examples, include: 3-(2-isopropylidene-hydrazino)-6-(2,4,5-trimethyl-imidazol-1-yl)-pyridazine, 3-(2-[2-methyl-pent-2-en-4-ylidene]-hydrazino)-6-(2-methyl-imidazol-1-yl)-pyridazine, 3-(2-[hepta-1,6-dien-4-ylidene]-hydrazino)-6-(2-methyl-imidazol-1-yl)-pyridazine, 3-(2-[2-methyl-pent-2-en-4-ylidene]-hydrazino)-6-(2-ethyl-imidazol-1-yl)-pyridazine, 3-hydrazino-6-(2-isopropyl-imidazol-1-yl)-pyridazine and 3-(2-isopropylidene-hydrazino)-6-(2-isopropyl-imidazol-1-yl)-pyridazine.

The novel compounds of the general formula I and their pharmacologically tolerated addition salts with acids possess pronounced blood pressure-lowering properties and may be used in the treatment of hypertonia.

Particularly active compounds include 3-hydrazino-6-(2-methyl-imidazol-1-yl)-pyridazine, 3-(2-isopropylidene-hydrazino)-6-(2-methyl-imidazol-1-yl)-pyridazine, 3-hydrazino-6-(2-ethyl-imidazol-1-yl)-pyridazine and 3-(2-isopropylidene-hydrazino)-6-(2-ethyl-imidazol-1-yl)-pyridazine.

The blood pressure-lowering action was demonstrated on narcotized rats (Sprague Dawley, weight: 230–280 g) under urethane-induced narcosis (1.78 g/kg administered intraperitoneally). The blood pressure was measured in the carotid aorta. The substance was administered into the jugular vein (using 1 ml/kg of an aqueous solution). The ED 20% was determined, as the dose producing a 20% lowering of blood pressure, from the linear regression between the logarithm of the dose (mg/kg) and the relative lowering of the blood pressure (Δ%).

The anti-hypertensive action was determined on spontaneously hypertonic rats (Okamoto). The substances were administered orally to groups of from 4 to 8 male animals. Before, and 2 hours after, administration, the systolic blood pressure was measured on the tail of the rat by means of a piezoelectric crystal sensor. The ED 20 was determined, as the dose which lowers the systolic pressure by 20%, from the linear regression between the logarithm of the dose (mg/kg) and the relative lowering of blood pressure (Δ%), with due account taken of the values found with placebo-treated control animals.

To determine the acute toxicity (LD 50), the substances were administered intraperitoneally to groups of 10 female NMRI mice (weighing 20–25 g each). The LD 50 was computed (by Probit analysis) as the dose after which 50% of the animals died within 7 days.

TABLE 1

Hypotensive and anti-hypertensive action, and toxicity

| Compound from Example No. | Hypotensive action(1) ED 20% mg/kg | R.E.(4) | Anti-hypertensive action(2) ED 20% mg/kg | R.E. | Toxicity(3) LD 50 mg/kg | R.E. | Therapeutic range Q |
|---|---|---|---|---|---|---|---|
| 1 a | 0.0310 | 2.75 | 1.41 | 4.86 | 193 | 1.06 | 137 |
| 1 c | 0.0638 | 1.34 | 2.91 | 2.35 | 156 | 1.32 | 53.6 |
| 2 a | 0.0464 | 1.84 | 2.46 | 2.78 | 98.6 | 2.09 | 40.1 |
| 2 b | 0.0464 | 1.84 | 2.48 | 2.76 | 124 | 1.66 | 50.1 |
| Dihydralazine | 0.0854 | 1.00 | 6.85 | 1.00 | 206 | 1.00 | 30.1 |

(1)Narcotized rats, intravenous administration
(2)Spontaneously hypertonic rats (SHR), oral administration
(3)Mice, intraperitoneal administration
(4)R.E. = relative effectiveness; dihydralazine = 1.00
(5)Q = $\frac{\text{LD 50 in mg/kg administered intraperitoneally}}{\text{ED 20\% in mg/kg administered orally}}$ As may be seen from the Table, the novel compounds lower the blood pressure of narcotized rats at doses which are lower, by a factor of from 1.3 (Example 1 c) to 2.8 (Example 1 a), than the dihydralazine doses. On wake spontaneously hypertonic rats, the substances are from 2.4 (Example 1 c) to 4.9 (Example 1 a) times as effective as dihydralazine. The toxic doses (LD 50) are from 40 (Example 2 a) to 137 (Example 1 a) times as great as the anti-hypertensive doses (whilst for dihydralazine the ratio is 30).

Accordingly, the present invention also relates to a therapeutic agent which contains a compound of the formula I, or a pharmacologically tolerated addition salt thereof with an acid, as the active compound, in addition to conventional excipients or diluents, and to the use of the compounds of the formula I for therapeutic purposes.

The therapeutic agents or formulations are prepared by compounding the active compound in a conventional manner, in particular by mixing, with the conventional pharmaceutical excipients or diluents and, where appropriate, conventional pharmaceutical auxiliaries, in accordance with the desired route of administration and in dosage units appropriate for the particular use.

For man, suitable doses are from 20 to 200 mg, preferably from 50 to 150 mg, and oral administration is preferred.

Examples of suitable forms for oral administration are tablets, film tablets, dragees, capsules, pills, powders, solutions, suspensions and forms which exert a depot effect.

For practical use, the compounds to be employed according to the invention are compounded with the liquid or solid excipients conventionally used in pharmaceutical production. For example, appropriate tablets can be obtained by mixing the active compound with conventional auxiliaries, for instance inert diluents, eg. dextrose, sugar, sorbitol, polyvinylpyrrolidone, mannitol, calcium carbonate, calcium phosphate or lactose, disintegrating agents, eg. corn starch, alginic acid or polyvinylpyrrolidone, binders, eg. starch or gelatin, lubricants, eg. magnesium stearate or talc, and/or agents for achieving a depot effect, eg. carboxypolymethylene, carboxymethylcellulose, cellulose acetate phthalate or polyvinyl acetate. The tablets may also consist of a plurality of layers. (cf. L. G. Goodman and A. Gilman, The Pharmaceutical Basis of Therapeutics).

Accordingly, dragees may be prepared by coating cores, prepared similarly to the tablets, with agents conventionally used in dragee coatings, eg. polyvinylpyrrolidone, shellac, gum arabic, talc, titanium dioxide or sugar. The dragee shell may also consist of several layers, in which the auxiliaries mentioned above in connection with tablets may be used.

The Examples which follow illustrate the invention.
Preparation of starting compounds.

EXAMPLE I

3-Chloro-6-(2-methyl-imidazol-1-yl)-pyridazine 104 millimoles of a 55% strength suspension of sodium hydride in paraffin oil are added, in portions, to 8.55 g (104 millimoles) of 2-methylimidazole in 80 ml of dimethylformamide, whilst stirring, the sodium salt being formed by continuing to stir the mixture for a further hour at room temperature, under nitrogen as a protective gas. 15.5 g (104 millimoles) of 3,6-dichloropyridazine are then added in portions to the reaction mixture, producing an exothermic reaction, with the temperature rising to 50°-60° C.; thereafter, stirring is continued for 5-10 hours at room temperature under nitrogen as a protective gas. When the mixture has cooled, the solvent is distilled off under about 0.5 mm Hg (using an oil pump), the residue is taken up in ice water, the aqueous solution is extracted with methylene chloride and the organic phase is washed repeatedly with water. The same yield is obtained if, after adding the 3,6-dichloropyridazine, the mixture is refluxed for 3-5 hours under nitrogen as the protective gas. The crude product obtained is purified by column chromatography on silica gel, with a 90:10 mixture of methylene chloride and methanol as eluant. Yield: 8.5 g (42%) of crystals, of melting point 104°-107° C.

We have found that even better yields are achieved on converse addition of the reactants. The 3,6-dichloropyridazine is introduced into dimethylformamide, and the Na salt of 2-methylimidazole, in dimethylformamide, is added in portions, with thorough stirring.

The following compounds are obtained by the method of Example I: 3-chloro-6-(imidazol-1-yl)-pyridazine, melting point 178°-180° C.; 3-chloro-6-(2-ethylimidazol-1-yl)-pyridazine, oil; 3-chloro-6-(2,4,5-trimethyl-imidazol-1-yl)-pyridazine, oil; and 3-chloro-6-(4-methyl-imidazol-1-yl)-pyridazine, melting point 165°-168° C.

Preparation of compounds according to the invention.

EXAMPLE 1

(a) 3-Hydrazino-6-(2-methyl-imidazol-1-yl)-pyridazine 6.7 g (35 millimoles) of 3-chloro-6-(2-methyl-imidazol-1-yl)-pyridazine are taken up in 30 ml of hydrazine hydrate and the mixture is heated for 5-10 hours at 100°-130° C. under nitrogen as a protective gas; the reaction mixture becomes homogeneous in the course of the first few hours. When the mixture has cooled, the crude product which has precipitated is filtered off. It is also possible to pour the reaction mixture into ice water and extract the mixture repeatedly with methylene chloride. Continuous extraction by means of a rotary perforator, using methylene chloride or chloroform as the extraction solvents, has also proved an advantageous method. Yet a further possibility is to distil off the hydrazine hydrate under reduced pressure.

The crude product obtained is taken up in hot isopropanol, after which the solution is advantageously concentrated and allowed to crystallize in the cold. 3-Hydrazino-6-(2-methyl-imidazol-1-yl)-pyridazine is purified by column chromatography on silica gel, using a 90:10 mixture of methylene chloride and methanol as the eluant, and is converted to the hydrochloride by reacting its solution in ethanol with a solution of hydrogen chloride in ether. Yield of dihydrochloride: 7.0 g (76%), melting point 280°-282° C. (with decomposition). The free base melts at 154°-156° C.

The following compounds are prepared by similar methods:

(b) 3-Hydrazino-6-(imidazol-1-yl)-pyridazine, melting point 199°-202° C.

(c) 3-Hydrazino-6-(2-ethyl-imidazol-1-yl)-pyridazine 0.5 H$_2$O, melting point 94°-97° C.

(d) 3-Hydrazino-6-(2,4,5-trimethyl-imidazol-1-yl)-pyridazine.4 HCl.2H$_2$O, melting point 64°-68° C.

(e) 3-Hydrazino-6-(4-methyl-imidazol-1-yl)-pyridazine.2 HCl, melting point 257°-260° C.

EXAMPLE 2

(a) 3-(2-Isopropylidene-hydrazino)-6-(2-methyl-imidazol-1-yl)-pyridazine 3.0 g (15.8 millimoles) of 3-hydrazino-6-(2-methyl-imidazol-1-yl)-pyridazine are suspended in 40 ml of acetone and the suspension is heated for 10 minutes on a steam bath under reflux.

The hot solution is then filtered.

On cooling, 3-(2-isopropylidene-hydrazino)-6-(2-methyl-imidazol-1-yl)-pyridazine, of melting point 173°-175° C., crystallizes out.

The following compounds are also prepared by this method:

(b) 3-(2-Isopropylidene-hydrazino)-6-(2-ethyl-imidazol-1-yl)-pyridazine, melting point 155°–156° C.

(c) 3-(2-Isopropylidene-hydrazino)-6-(4-methyl-imidazol-1-yl)-pyridazine, melting point 224°–226° C.

Examples of pharmaceutical use.

1. TABLETS

| | |
|---|---|
| Active compound | 60 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 290 mg |

The active compound is moistened with a 10% strength aqueous solution of the polyvinylpyrrolidone, forced through a 1.0 mm mesh sieve and dried at 50° C. These granules are mixed with the polyethylene glycol (mean molecular weight 4,000), hydroxypropylmethyl-cellulose, talc and magnesium stearate, and the mixture is pressed to form tablets each weighing 290 mg.

2. EXAMPLE OF DRAGEES

| | |
|---|---|
| Active compound | 90 mg |
| Lactose | 90 mg |
| Corn starch | 60 mg |
| Polyvinylpyrrolidone | 6 mg |
| Magnesium stearate | 1 mg |
| | 247 mg |

The mixture of the active compound with lactose and corn starch is moistened with an 8% strength aqueous solution of the polyvinylpyrrolidone and passed through a 1.5 mm mesh sieve, and the granules obtained are dried at 50° C. and forced through a 1.0 mm mesh sieve. The granules thus obtained are mixed with magnesium stearate and the mixture is pressed to form dragee cores. These cores are then provided, in a conventional manner, with a coating substantially consisting of sugar and talc.

We claim:
1. 3-Hydrazino-6-(2-methyl-imidazol-1-yl)-pyridazine.
2. 3-Hydrazino-6-(2-ethyl-imidazol-1-yl)-pyridazine.
3. 3-(2-Isopropylidene-hydrazino)-6-(2-methyl-imidazol-1-yl)-pyridazine.
4. 3-(2-Isopropylidene-hydrazino)-6-(2-ethyl-imidazol-1-yl)-pyridazine.
5. A therapeutic agent for the treatment of hypertonia which comprises an effective amount of a compound of claim 1, 2, 3 or 4 or a physiologically tolerated additional salt thereof with an acid for lowering blood pressure combined with a pharmaceutically acceptable excipient and/or diluent.

* * * * *